US00PP14633P39

(12) United States Plant Patent
Moser

(10) Patent No.: US PP14,633 P3
(45) Date of Patent: Mar. 23, 2004

(54) CHRYSANTHEMUM PLANT NAMED 'MOZA VES 02'

(50) Latin Name: *Chrysanthemum morifolium*
Varietal Denomination: Moza Ves 02

(75) Inventor: Frank Moser, Alva, FL (US)

(73) Assignee: Mozant, LLC, Oxnard, CA (US)

( * ) Notice: Subject to any disclaimer, the term of this patent is extended or adjusted under 35 U.S.C. 154(b) by 0 days.

(21) Appl. No.: 10/136,824

(22) Filed: Apr. 30, 2002

(65) Prior Publication Data

US 2003/0204888 P1 Oct. 30, 2003

(51) Int. Cl.[7] ..... A01H 5/00
(52) U.S. Cl. ..... Plt./287
(58) Field of Search ..... Plt./287

(56) References Cited

U.S. PATENT DOCUMENTS

PP11,866 P2 5/2001 Moser ..... Plt./286

OTHER PUBLICATIONS

Chrysanthemum once again Horticulture Science Dick Brummitt.*

* cited by examiner

*Primary Examiner*—Bruce R. Campell
*Assistant Examiner*—Annette H Para
(74) *Attorney, Agent, or Firm*—Knobbe, Martens, Olson & Bear, LLP

(57) ABSTRACT

A new and distinct Chrysanthemum plant cultivar is disclosed, characterized by a daisy-type inflorescence, consistent flowering response to short days, blooming consistently after 49 days of short day length, free branching habit, purple ray florets with a lighter colored area at the tip, a very uniform round growth habit, and a large quantity of blooms per flowering branch.

1 Drawing Sheet

Latin name of the genus and species: The present invention relates to a new and distinct cultivar of Chrysanthemum plant, botanically known as *Chrysanthemum morifolium.*

Variety denomination: The new and distinct Chrysanthemum plant is hereinafter referred to by the cultivar name 'Moza Ves 02.'

BACKGROUND OF THE INVENTION

The new cultivar is a product of hybridization of a female parent Chrysanthemum plant variety 'MZ-312' (undistributed in the United States) and a male parent Chrysanthemum plant variety 'MZ-33' (undistributed in the United States). The new cultivar was discovered and selected by the inventor in October 1998.

Asexual reproduction of the new cultivar by apical tip cutting and meristem tissue culture was performed in Oxnard, Calif. and has shown that the unique features of this cultivar are stable and reproduced true to type on successive generations.

SUMMARY OF THE INVENTION

The cultivar 'Moza Ves 02' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'Moza Ves 02.' These characteristics in combination distinguish 'Moza Ves 02' as a new and distinct Chrysanthemum cultivar:

1. Daisy-type inflorescence,
2. Consistent flowering response to short days, blooming consistently after 49 days of short day length,
3. Free branching habit, 4. Purple ray florets with a lighter colored area at the tip,
5. Very uniform round growth habit, and
6. Large quantity of blooms per flowering branch.

Plants of the new cultivar are similar to plants of the female parent variety, 'MZ-312' in most horticultural characteristics, however plants of the new cultivar have a ray florets of a different color, have a different type of inflorescence, and have a more round plant form than plants of the female parent variety.

Plants of the new cultivar are similar to plants of the male parent variety, 'MZ-33' in most horticultural characteristics, however plants of the new cultivar have a different type of inflorescence and a more flexible plant type than plants of the male parent variety. Plants of the new cultivar also bloom naturally two weeks earlier than plants of the male parent variety.

In comparison to the commercially available variety 'Temptress' (U.S. Plant Pat. No. 11,866), 'Moza Ves 02' has a smaller diameter disc, fewer disc flowers per inflorescence, purple ray florets with a white tip, and more inflorescences per flowering branch.

BRIEF DESCRIPTION OF THE PHOTOGRAPH

The photograph shows a plant of 'Moza Ves 02' grown in a six-inch container. One cutting was used in the pot.

DETAILED BOTANICAL DESCRIPTION

In the following description, color references are made to The Royal Horticultural Society Colour Chart except where general terms of ordinary dictionary significance are used. The following observations and measurements describe 68 day old plants grown in Oxnard, Calif. during the month of December and January. The growing temperature ranged from 55° to 68° F. at night to 60° to 75° F. during the day.

Measurements and numerical values represent averages of typical flowering types.

Botanical classification: *Chrysanthemum morifolium* cultivar 'Moza Ves 02'.
Commercial classification: Garden-type Chrysanthemum.
Parentage: Hybridization of a female parent Chrysanthemum plant variety, 'MZ-312' (undistributed in the United States), and a male parent Chrysanthemum plant variety 'MZ-33' (undistributed in the United States).

PROPAGATION

Time to rooting: 7 to 14 days at approximately 21° C.
Rooting habit: Fine, fibrous.

PLANT

Growth habit: Mounding herbaceous perennial.
Height: Approximately 13 cm.
Spread: Approximately 12.5 cm.
Growth rate: Moderate.
Branching characteristics: Free Branching.
Length of lateral branches: Approximately 14 cm.
Number of leaves per lateral branch: Approximately 19.

FOLIAGE

Leaf:
- *Arrangement.*—Alternate.
- *Average length.*—Approximately 5.6 cm.
- *Average width.*—Approximately 3.1 cm.
- *Shape of blade.*—Ovate.
- *Apex.*—Cuspidate.
- *Base.*—Attenuate.
- *Attachment.*—Stalked.
- *Margin.*—Palmately lobed.
- *Texture of top surface.*—Lightly pubescent.
- *Texture of bottom surface.*—Lightly pubescent.
- *Color.*—Young foliage upper side: Near 139A. Young foliage under side: Near 137C. Mature foliage upper side: Near 137A. Mature foliage under side: Near 137C. Venation upper side: Near 138C. Venation under side: Near 137B.
- *Type.*—Net.

Petiole:
- *Average length.*—Approximately 1.7 cm.
- *Color.*—Near 138B.
- *Diameter.*—Approximately 0.25 cm.

BLOOM

Inflorescence:
- *Flowering habit.*—Induced by darkness period greater than 13.5 hours, approximately 49 days of appropriate day length required to induce and develop blooms.
- *Inflorescence form.*—Daisy.
- *Natural flowering season.*—Approximately the first week of September.
- *Number of inflorescences per lateral branch.*—Approximately 16.
- *Inflorescence diameter.*—Approximately 3.7 cm.
- *Inflorescence depth.*—Approximately 2 cm.
- *Inflorescence longevity on plant.*—Approximately 3.0 days.
- *Persistence.*—Persistent.
- *Disc diameter.*—Approximately 0.5 cm.

Ray florets:
- *Appearance.*—Matte.
- *Texture.*—Smooth.
- *Average number per flower.*—111.
- *Shape.*—Oblanceolate.
- *Aspect.*—Flat.
- *Margin.*—Entire.
- *Apex.*—Retuse.
- *Length.*—Approximately 1.9 cm.
- *Width.*—Approximately 0.5 cm.
- *Color.*—Upper surface at first opening: Near 77B with near 76D along apex. Upper surface at maturity: Near 71A with near 76D along apex. Upper surface at fading: Near 77A with near 76D along apex. Under surface at first opening: Near 77B. Under surface at maturity: Near 84B. Under surface at fading: Near 82C.

Disc florets:
- *Appearance.*—Shiny.
- *Texture.*—Smooth.
- *Average number per flower.*—Approximately 17.
- *Shape.*—Cylindrical.
- *Apex.*—Obtuse.
- *Average length.*—Approximately 0.5 cm.
- *Average width.*—Approximately 0.1 cm.
- *Color.*—At first opening: Near 6A. At maturity: Near 7A. At fading: Near 12A.

Peduncle:
- *Length.*—At terminal end (shortest): Approximately 4.2 cm. At lateral end (longest): Approximately 8.7 cm.
- *Angle to stem.*—Acute.
- *Strength.*—Moderate.
- *Color.*—Near 138A.
- *Habit.*—Upright.
- *Diameter.*—Approximately 0.2 cm.
- *Texture.*—Pubescent.
- *Internode length.*—Approximately 3.1 cm.

Inflorescence bud:
- *Length.*—Approximately 0.8 cm.
- *Diameter.*—Approximately 0.8 cm.
- *Form.*—Globular.
- *Color.*—Near 84B.

Involucral bracts (phyllaries):
- *Appearance.*—Matte.
- *Texture.*—Lightly pubescent.
- *Number.*—Approximately 24.
- *Shape.*—Oblanceolate.
- *Margin.*—Entire.
- *Apex.*—Acute.
- *Length.*—Approximately 0.7 cm.
- *Width.*—Approximately 0.3 cm.
- *Color.*—Upper side: Near 138A.

REPRODUCTIVE ORGANS

Ray florets:
- *Pistillate.*—Number of pistils per flower: 1. Stigma shape: 2 branched. Stigma color: Near 7A. Style color: Near 154D. Style length: Approximately 0.4 cm.

Disc florets (hermaphroditic):
- *Pistillate.*—Number of pistils per flower: 1. Stigma shape: Two-branched. Stigma color: Near 7B. Style length: Approximately 0.4 cm. Style color: Near 154D.
- *Staminate.*—Number of stamens per flower: 5. Anther shape: Tubular. Anther color: Near 13A.
- *Pollen.*—No pollen detected.

OTHER CHARACTERISTICS

Seed production: Commercially, this plant is not used or observed in a stage wherein seeds would be produced. Therefore, seed production has not been observed.

Disease resistance: Neither resistance nor susceptibility has been observed.

Cold tolerance: Flowering plants are resistant to cold to approximately 0° C. Non-flowering plants have been observed to withstand cold temperatures to approximately −4° C.

Drought tolerance: Plants will come back with little damage from a full wilt. Plants usually will not tolerate prolonged drought (over 7 days without any water).

What is claimed is:

1. A new and distinct cultivar of Chrysanthemum plant named 'Moza Ves 02' as herein illustrated and described.

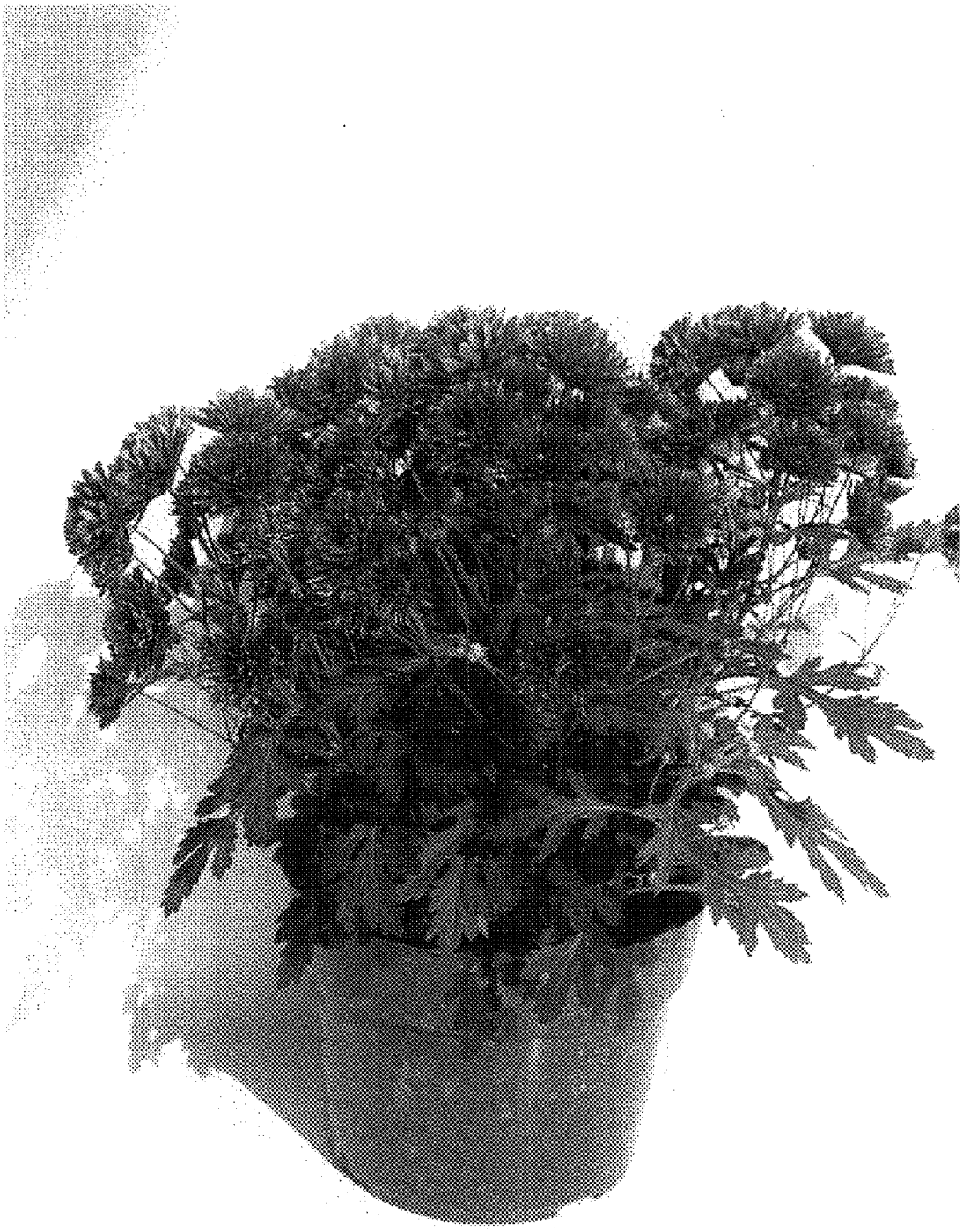

* * * * *